United States Patent
Wang et al.

(10) Patent No.: US 9,944,689 B2
(45) Date of Patent: Apr. 17, 2018

(54) HUMAN CTLA4 MUTANTS AND USE THEREOF

(71) Applicant: THE GENERAL HOSPITAL CORPORATION, Boston, MA (US)

(72) Inventors: Zhirui Wang, Malden, MA (US); Christene A. Huang, Dover, MA (US); David H. Sachs, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 228 days.

(21) Appl. No.: 14/773,056

(22) PCT Filed: Mar. 5, 2014

(86) PCT No.: PCT/US2014/020626
§ 371 (c)(1),
(2) Date: Sep. 4, 2015

(87) PCT Pub. No.: WO2014/138188
PCT Pub. Date: Sep. 12, 2014

(65) Prior Publication Data
US 2016/0017018 A1    Jan. 21, 2016

Related U.S. Application Data

(60) Provisional application No. 61/774,350, filed on Mar. 7, 2013.

(51) Int. Cl.
| *C07K 14/705* | (2006.01) |
| *A61K 38/17* | (2006.01) |
| *A61K 39/00* | (2006.01) |
| *A61K 39/395* | (2006.01) |
| *C07K 16/18* | (2006.01) |
| *A61K 38/00* | (2006.01) |

(52) U.S. Cl.
CPC .... *C07K 14/70521* (2013.01); *A61K 38/1774* (2013.01); *A61K 39/001* (2013.01); *A61K 39/3955* (2013.01); *C07K 16/18* (2013.01); *A61K 38/00* (2013.01); *A61K 2039/505* (2013.01); *A61K 2039/577* (2013.01); *A61K 2039/6056* (2013.01); *C07K 2317/52* (2013.01); *C07K 2319/30* (2013.01)

(58) Field of Classification Search
None
See application file for complete search history.

(56) References Cited

U.S. PATENT DOCUMENTS

| 4,522,811 | A | 6/1985 | Eppstein et al. |
| 4,818,700 | A | 4/1989 | Cregg et al. |
| 5,434,131 | A | 7/1995 | Linsley et al. |
| 5,844,095 | A | 12/1998 | Linsley et al. |
| 5,851,795 | A | 12/1998 | Linsley et al. |
| 5,885,579 | A | 3/1999 | Linsley et al. |
| 5,885,796 | A | 3/1999 | Linsley et al. |
| 5,968,510 | A | 10/1999 | Linsley et al. |
| 5,977,318 | A | 11/1999 | Linsley et al. |
| 6,803,225 | B2 | 10/2004 | Contreras et al. |
| 7,029,872 | B2 | 4/2006 | Gerngross |
| 7,105,166 | B1 | 9/2006 | Linsley et al. |
| 7,252,933 | B2 | 8/2007 | Contreras et al. |
| 7,326,681 | B2 | 2/2008 | Gerngross |
| 7,432,344 | B1 * | 10/2008 | Lechler ............. A01K 67/0275 530/350 |
| 7,449,308 | B2 | 11/2008 | Gerngross et al. |
| 7,479,389 | B2 | 1/2009 | Nett et al. |
| 7,507,573 | B2 | 3/2009 | Contreras et al. |
| 7,514,253 | B2 | 4/2009 | Nett |
| 2003/0086940 | A1 * | 5/2003 | Costa ................ C07K 14/70521 424/185.1 |
| 2005/0169919 | A1 * | 8/2005 | Linsley ............ C07K 14/70521 424/144.1 |
| 2008/0305988 | A1 * | 12/2008 | Coia ................ C07K 14/70521 514/1.1 |
| 2009/0012400 | A1 | 1/2009 | Guracar et al. |
| 2009/0186097 | A1 * | 7/2009 | Ayares .................. C12N 15/85 424/572 |
| 2011/0201052 | A1 | 8/2011 | Raitano et al. |
| 2015/0104450 | A1 * | 4/2015 | Minter ............. C07K 14/70521 424/134.1 |

FOREIGN PATENT DOCUMENTS

| WO | WO 2009/085135 | 7/2009 |
| WO | WO 2011/046855 | 4/2011 |

OTHER PUBLICATIONS

Ansari et al. Immunology Letters (2017) 183: 8-16.*
Baroja-Mazo et al. World J Gastroenterol. (2016) 22: 7676-7691.*
Cooper et al. International Journal of Surgery (2015) 23: 211-216.*
Darlington et al. J Immunol (2005) 175: 996-1004.*
El-Charabaty et al. Expert Rev. Clin. Immunol. (2012) 8: 527-536.*
Gerstmayer et al. FEBS Letters (1997) 407: 63-68.*
Griesemer et al. Immunol Rev. (2014) 258: 241-258.*
Hufton et al. FEBS Letters (2000) 475: 225-231.*
Kawai et al. American Journal of Transplantation (2014) 14: 1599-1611.*
Larsen et al. American Journal of Transplantation (2005) 5: 443-453.*
Peraino et al. Protein Expression and Purification (2012) 82: 270-278.*
Peraino et al. Hum Immunol. (2013) 74(7): 842-848.*
Peraino et al. Journal of Immunological Methods (2013) 391: 103-111.*
Sachs D. Arch Surg. (2011) 146: 501-505.*
Salisbury et al. Pediatr Nephrol (2014) 29: 2263-2272.*
Su et al. Ann Pharmacother. (2012) 46: 57-67.*
Vagefi et al. International Journal of Surgery (2015) 23: 291-295.*
Vaughan et al. J Immunol (2000) 165: 3175-3181.*

(Continued)

*Primary Examiner* — Ilia Ouspenski
(74) *Attorney, Agent, or Firm* — Fish & Richardson P.C.

(57) ABSTRACT

Mutant forms of human CTLA4, and their use, e.g., in xenotransplantation.

19 Claims, 6 Drawing Sheets

(56) References Cited

OTHER PUBLICATIONS

Figure 2B:
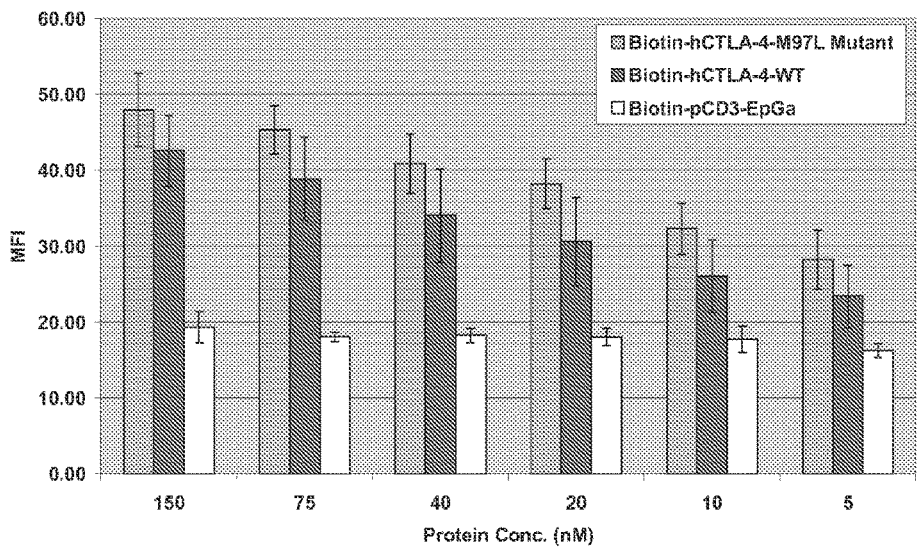

Weninger et al. Journal of Biotechnology (2016) 235: 139-149.*
Yamada et al. Curr Opin Organ Transplant. (2012) 17: 168-173.*
Zhu et al. Developmental and Comparative Immunology (2011) 35: 736-744.*
Bobrowicz et al., "Isolation of three contiguous genes, ACR1, ACR2 and ACR3, involved in resistance to arsenic compounds in the yeast *Saccharomyces cerevisiae*," Yeast, Jul. 1997, 13(9):819-828.
Bollok et al., "Recent Patents on the *Pichia Pastoris* Expression System: Expanding the Toolbox for Recombinant Protein Production," Recent Patents on Biotechnology, 2009, 3, 192-201.
Bour-Jordan et al., "Intrinsic and extrinsic control of peripheral T-cell tolerance by costimulatoly molecules of the CD28/ B7 family," Immunol Rev, May 2011, 241(1):180-205.
Cereghino and Cregg, "Heterologous protein expression in the methylotropic yeast Pichia pastoris," FEMS Microbiology Reviews, 2000, 24:45-66.
Cereghino et al, "New selectable marker/auxotrophic host strain combinations for molecular genetic manipulation of Pichia pastoris," Gene, Jan. 24, 2001, 263:159-169.
Chikuma et al., "B7-independent inhibition of T cells by CTLA-4," The Journal of Immunology, 2005; 175:177-81.
Cho et al., "Establishment of transplantable porcine tumor cell lines derived from MHC-inbred miniature swine," Blood, Dec. 2007; 110: 3996-4004.
Cosano et al., "Cloning and Sequence Analysis of the Pichia pastoris TRP1, IPP1 and HIS3 Genes," Yeast, 1998, 14:861 -867.
Cregg, "Pichia pastoris as a host system for transformations," Molecular and Cellular Biology, Dec. 1985, 5(12): 3376-3385.
Cregg, "Methods in Molecular Biology: Pichia Protocols," Second Edition, Humana Press, 2007, 15:17-26.
Henikoff et al., "Amino acid substitution matrices from protein blocks," Proc Natl Acad Sci, Nov. 15, 1992, vol. 89(22): 10915-10919.
Ilgen et al., (2004) Chapter 7: Pichia pastoris. In: Production of recombinant proteins: microbial and eukaryotic expression systems. Gellissen, G. (ed.) Wiley-VCH Verlag, Weinheim, Germany, pp. 143-162.

International Preliminary Report on Patentability in International Application No. PCT/US14/20626, dated Sep. 8, 2015, 11 pages.
International Search Report and Written Opinion in International Application No. PCT/US14/20626, dated Jun. 2, 2014, 14 pages.
Larsen et al., "Rational Development of LEA29Y (belatacept), a High-Affinity variant of CTLA4-Ig with Potent Immunosuppressive Properties," 2005, Am J Transplant, 5:443-53.
Lei et al., "Structure-function analysis of human glucose-6-phosphatase, the enzyme deficient in glycogen storage disease type 1a," J Biol Chem , May 19, 1995; 270(20):11882-6.
Morton et al., "Differential effects of CTLA-4 substitutions on the binding of human CD80 (B7-1) and CD86 (B7-2)," J Immunol Feb. 1, 1996; 156(3):1047-54.
Pentcheva-Hoang , "B7-1 and B7-2 selectively recruit CTLA-4 and CD28 to the immunological synapse," Immunity, Sep. 2004, 21:401-13.
Peraino et al., "Expression and purification of soluble porcine CTLA-4 in yeast Pichia pastoris," Protein Expr Purif, 2012, 82:270-8.
Phelps et al., "Production and characterization of transgenic pigs expressing porcine CTLA4-Ig," Xenotransplantation, Nov.-Dec. 2009;16(6):477-85.
Riha and Rudd, "CD28 co-signaling in the adaptive immune response," Self/Nonself, 2010; 1(3):231-240.
Romanos et al., "Foreign Gene Expression in Yeast: a Review," Yeast, 1992, 8:423-488.
Sansom, "CD28, CTLA-4 and their ligands: who does what and to whom?," Immunology 2000; 101:169-177.
Takada et al., The Role of the B7 Costimulatoly Pathway in Experimental Cold Ischemia/Reperfusion Injury, J Clin Invest, Sep. 1997, 100(5):1199-203.
Vaughan, "Porcine CTLA4-Ig lacks a MYPPPY motif, binds inefficiently to human B7 and specifically suppresses human CD4+ T cell responses costimulated by pig but not human B7," J Immunol, 2000; 165(6):3175-81.
Woo et al., "Gene optimization is necessary to express a bivalent anti-human anti-T cell immunotoxin in Pichia pastoris," Protein Expression and Purification, Jul. 2002, 25(2): 270-282.
Wysocki et al, The *Saccharomyces cerevisiae* ACR3 Gene Encodes a Putative Membrane Protein Involved in Arsenite Transport J-Biol. Chem., 1997, 272(48):30061-30066.

* cited by examiner

Figure 1A  FACS Binding Analysis Using Human CD80+ AML Tumor Cells
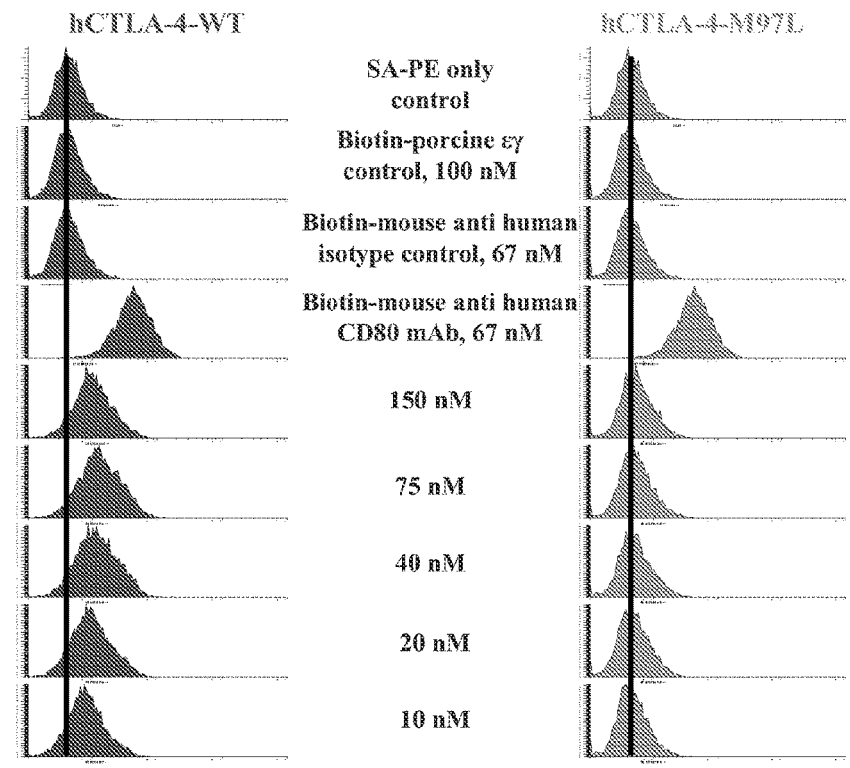
Figure 1B
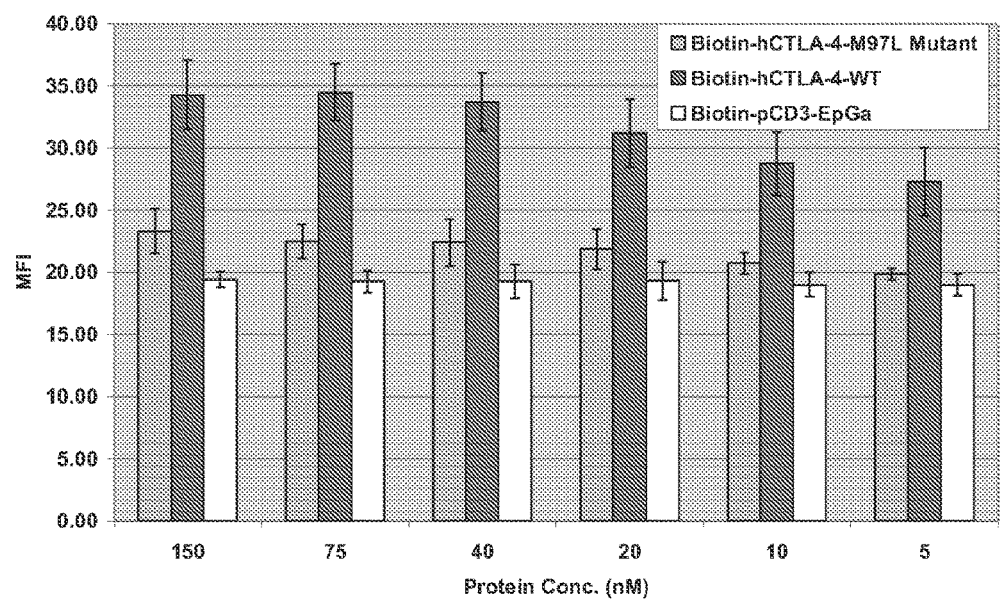

Figure 1C  FACS blocking analysis of mouse anti-human CD80
mAb (67 nM) using human CD80+ AML tumor cells
Competitor: wild-type or M97L mutant
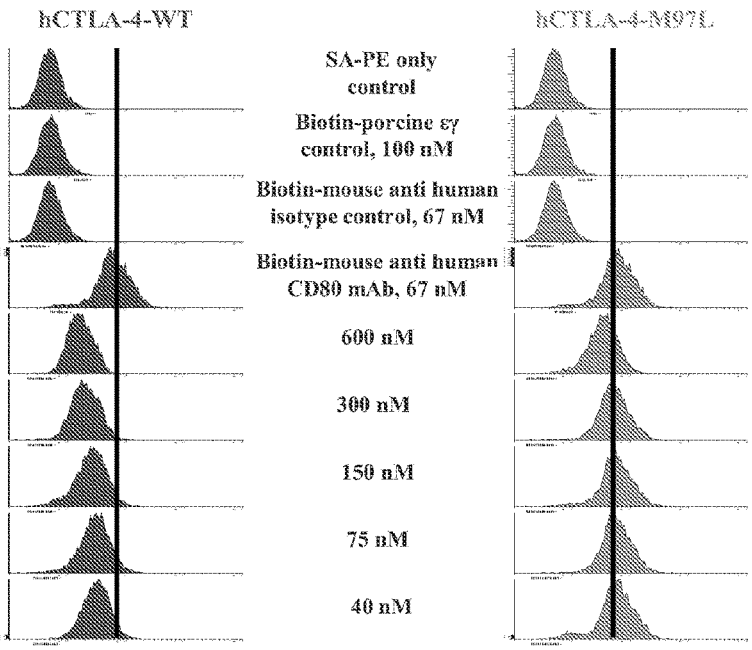
Figure 2A  FACS Binding Analysis Using Porcine CD80+ LCL
13271 Cells
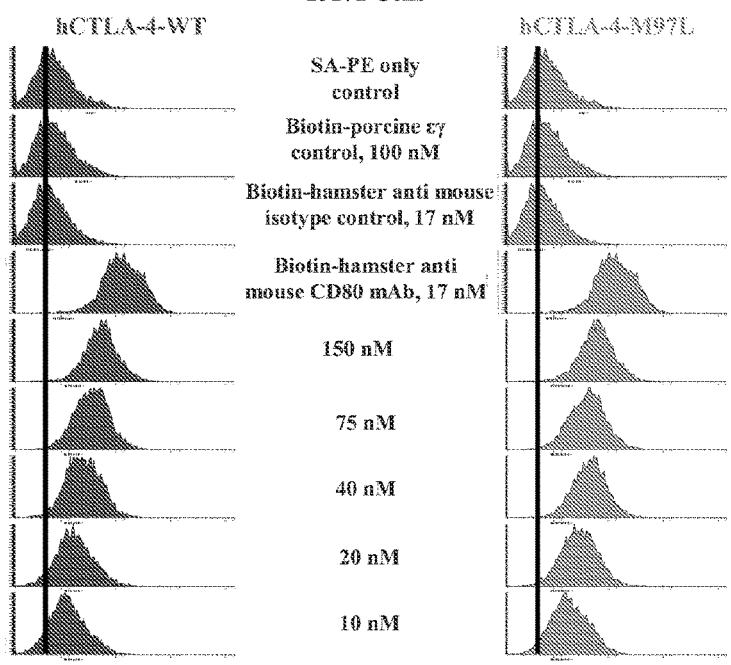

FACS blocking analysis of hamster anti-CD80 mAb
(17 nM) using porcine CD80+ LCL 13271 cells
Competitor: wild-type or M97L mutant Figure 3A    FACS Binding Analysis Using Human CD80+ AML Tumor Cells
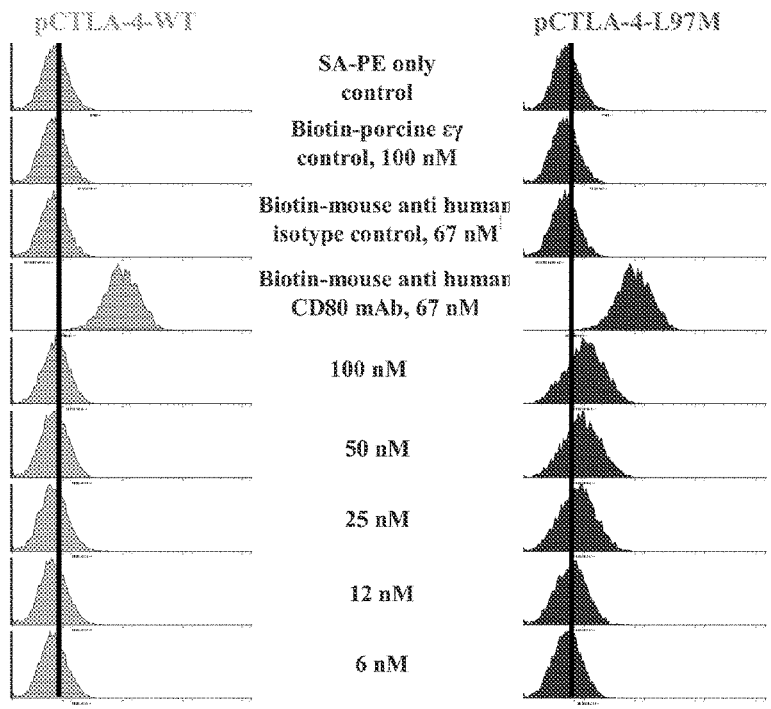
Figure 3B
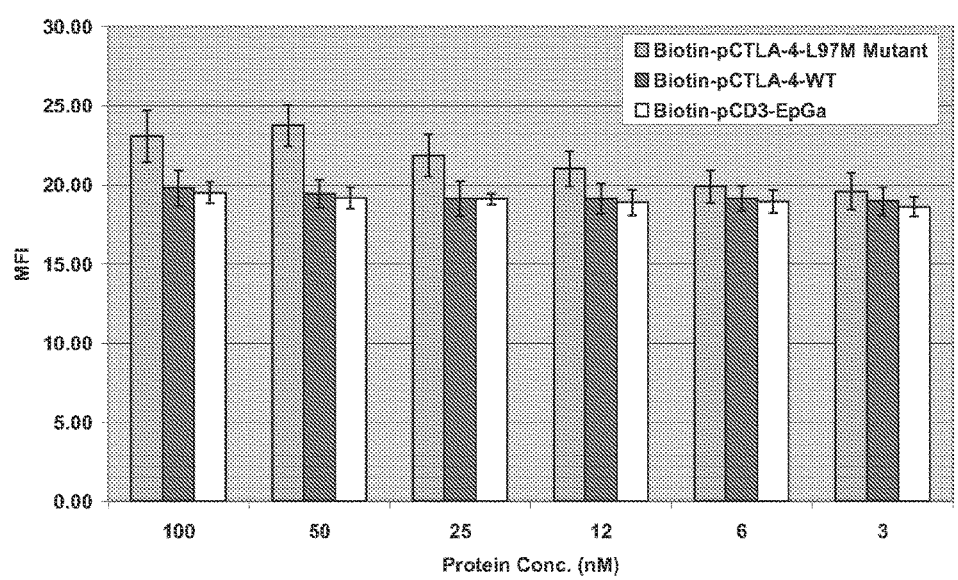

Figure 3C    FACS blocking analysis of mouse anti-human CD80
mAb (67 nM) using human CD80+ AML tumor cells
Competitor: wild-type or L97M mutant
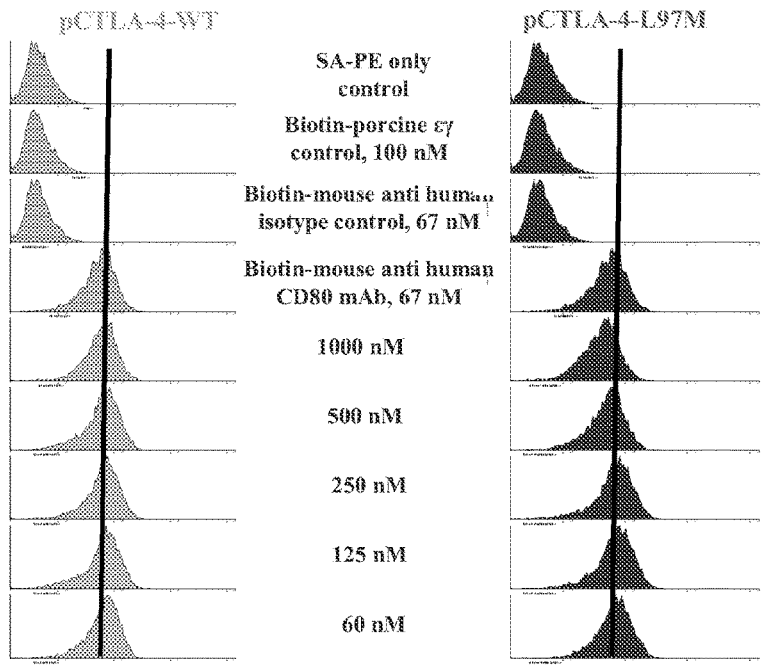
Figure 4A    FACS Binding Analysis Using Porcine CD80+ LCL 13271
Cells
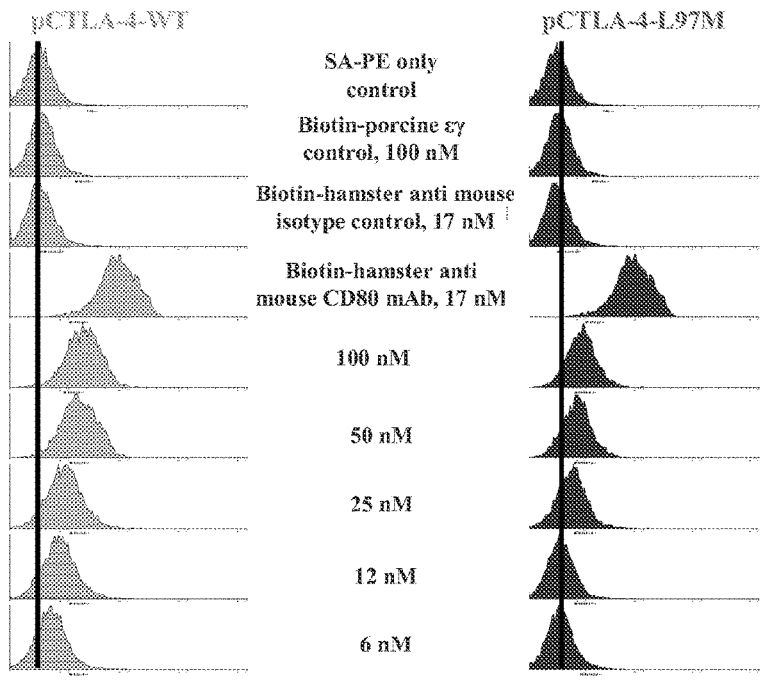

Figure 4C  FACS blocking analysis of hamster anti-CD80 mAb
(17 nM) using porcine CD80+ LCL 13271 cells
Competitor: wild-type or L97M mutant

SEQUENCE LISTING

```
<160> NUMBER OF SEQ ID NOS: 13

<210> SEQ ID NO 1
<211> LENGTH: 161
<212> TYPE: PRT
<213> ORGANISM: Artificial Sequence
<220> FEATURE:
<223> OTHER INFORMATION: mutant human CTLA-4

<400> SEQUENCE: 1

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Leu Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp

<210> SEQ ID NO 2
<211> LENGTH: 8
<212> TYPE: PRT
<213> ORGANISM: Artificial Sequence
<220> FEATURE:
<223> OTHER INFORMATION: peptide tag sequence

<400> SEQUENCE: 2

Asp Tyr Lys Asp Asp Asp Asp Lys
1               5
```

```
<210> SEQ ID NO 3
<211> LENGTH: 6
<212> TYPE: PRT
<213> ORGANISM: Artificial Sequence
<220> FEATURE:
<223> OTHER INFORMATION: peptide tag sequence

<400> SEQUENCE: 3

Tyr Pro Tyr Asp Val Pro
 1               5

<210> SEQ ID NO 4
<211> LENGTH: 10
<212> TYPE: PRT
<213> ORGANISM: Artificial Sequence
<220> FEATURE:
<223> OTHER INFORMATION: peptide tag sequence

<400> SEQUENCE: 4

Ile Leu Lys Lys Ala Thr Ala Tyr Ile Leu
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: peptide tag sequence

<400> SEQUENCE: 5

Glu Gln Lys Leu Ile Ser Glu Glu Asp Leu
 1               5                  10

<210> SEQ ID NO 6
<211> LENGTH: 45
<212> TYPE: DNA
<213> ORGANISM: Artificial Sequence
<220> FEATURE:
<223> OTHER INFORMATION: PCR primers

<400> SEQUENCE: 6
tacatctgta aggtcgaatt gatgtaccca cctccatact acgtt            45

<210> SEQ ID NO 7
<211> LENGTH: 45
<212> TYPE: DNA
<213> ORGANISM: Artificial Sequence
<220> FEATURE:
<223> OTHER INFORMATION: PCR primers

<400> SEQUENCE: 7
aacgtagtat ggaggtgggt acatcaattc gaccttacag atgta            45

<210> SEQ ID NO 8
<211> LENGTH: 45
<212> TYPE: DNA
<213> ORGANISM: Artificial Sequence
<220> FEATURE:
<223> OTHER INFORMATION: PCR primers

<400> SEQUENCE: 8
tacatttgta aggttgagtt gttgtaccca cctccatact acttg            45

<210> SEQ ID NO 9
<211> LENGTH: 45
<212> TYPE: DNA
<213> ORGANISM: Artificial Sequence
```

<220> FEATURE:
<223> OTHER INFORMATION: PCR primers

<400> SEQUENCE: 9
caagtagtat ggaggtgggt acaacaactc aaccttacaa atgta          45

<210> SEQ ID NO 10
<211> LENGTH: 132
<212> TYPE: PRT
<213> ORGANISM: Artificial Sequence
<220> FEATURE:
<223> OTHER INFORMATION: mutant Non-N-Glycosylated soluble human
      CTLA-4-6xHis amino acid sequence (aa 36-161)

<400> SEQUENCE: 10

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Ala Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Ala Gly Thr
            100                 105                 110

Gln Ile Tyr Val Ile Asp Pro Glu Pro Cys Pro Asp Ser Asp His His
        115                 120                 125

His His His His
    130

<210> SEQ ID NO 11
<211> LENGTH: 396
<212> TYPE: DNA
<213> ORGANISM: Artificial Sequence
<220> FEATURE:
<223> OTHER INFORMATION: mutant Non Non-N-Glycosylated soluble human
      CTLA-4-6xHis DNA sequence

<400> SEQUENCE: 11
aaggctatgc acgttgctca accagctgtt gtcttggctt cttccagagg tattgcttct     60
ttcgtttgtg agtacgcttc tccaggtaag gctactgagg ttagagttac tgtcttgaga    120
caagctgact ctcaagttac tgaggtttgt gctgctactt acatgatggg taacgagttg    180
actttcttgg acgactctat tgtactggt acttcttccg gtaaccaagt tgctttgact     240
attcaaggtt tgagagctat ggacactggt ttgtacattt gtaaggttga gttgatgtac    300
ccacctccat actacttggg tattggtgct ggtactcaaa tttacgttat tgacccagag    360
ccttgtccag actctgacca ccaccaccac caccac                              396

<210> SEQ ID NO 12
<211> LENGTH: 132
<212> TYPE: PRT
<213> ORGANISM: Artificial Sequence
<220> FEATURE:
<223> OTHER INFORMATION: mutant Non-N-Glycosylated soluble human
      CTLA-4-M97L-6xHis amino acid sequence (aa 36-161)

```
<400> SEQUENCE: 12

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
                20                  25                  30

Glu Val Arg Val Thr Val Leu Arg Gln Ala Asp Ser Gln Val Thr Glu
            35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Ala Leu Thr
65                  70                  75                  80

Ile Gln Gly Leu Arg Ala Met Asp Thr Gly Leu Tyr Ile Cys Lys Val
                85                  90                  95

Glu Leu Leu Tyr Pro Pro Pro Tyr Tyr Leu Gly Ile Gly Ala Gly Thr
            100                 105                 110

Gln Ile Tyr Val Ile Asp Pro Glu Pro Cys Pro Asp Ser Asp His His
            115                 120                 125

His His His His
    130

<210> SEQ ID NO 13
<211> LENGTH: 396
<212> TYPE: DNA
<213> ORGANISM: Artificial Sequence
<220> FEATURE:
<223> OTHER INFORMATION: mutant Non-N-Glycosylated soluble human
      CTLA-4-M97L-6xHis DAN sequence

<400> SEQUENCE: 13
aaggctatgc acgttgctca accagctgtt gtcttggctt cttccagagg tattgcttct      60
ttcgtttgtg agtacgcttc tccaggtaag gctactgagg ttagagttac tgtcttgaga    120
caagctgact ctcaagttac tgaggtttgt gctgctactt acatgatggg taacgagttg    180
actttcttgg acgactctat ttgtactggt acttcttccg gtaaccaagt tgctttgact    240
attcaaggtt tgagagctat ggacactggt ttgtacattt gtaaggttga gttgttgtac    300
ccacctccat actacttggg tattggtgct ggtactcaaa tttacgttat tgacccagag    360
ccttgtccag actctgacca ccaccaccac caccac                              396
```

HUMAN CTLA4 MUTANTS AND USE THEREOF

CLAIM OF PRIORITY

This application is a U.S. National Phase Application under 35 U.S.C. § 371 of International Patent Application No. PCT/US2014/020626, filed on Mar. 5, 2014, which claims the benefit of U.S. Patent Application Ser. No. 61/774,350, filed on Mar. 7, 2013. The entire contents of the foregoing are hereby incorporated by reference.

TECHNICAL FIELD

This invention relates to mutant forms of human CTLA4, and their use, e.g., in xenotransplantation.

BACKGROUND

T cell activation occurs following two molecular interactions commonly referred to as signal one and signal two. Signal one comes from the antigenic peptide-MHC complex interacting with the T cell receptor (TCR) and signal two describes a series of co-stimulatory receptors on antigen presenting cells (APCs) such as the CD28/CTLA-4-CD80/CD86 co-stimulation pathway Riha and Rudd, Self Nonself 2010; 1:231-240; Sansom, Immunology 2000; 101:169-177). Blocking either signal can halt T cell activation.

SUMMARY

The binding motif of human CTLA-4 is known to be MYPPPY and for porcine CTLA-4 the binding motif is LYPPPY. Is this single amino acid difference of methionine (Met, M) versus leucine (Leu, L) critical for the CTLA-4 binding? The recombinant soluble porcine CTLA-4 is incapable of binding to human CD80 (Peraino et al., Protein Expr Purif 2012; 82:270-8). In the experiments described herein Leu was mutated to Met at the binding motif of the soluble porcine CTLA-4 and Met was mutated to Leu at the binding motif of the soluble human CTLA-4 and the effects of these mutations was then analyzed on both porcine and human CD80+ cells. The soluble porcine CTLA-4-L97M mutant decreased the binding affinity to porcine CD80 compared to the wild-type and conferred weak binding to human CD80, which indicates that the Leu at the binding motif of porcine CTLA-4 is important, but not as critical, for determining binding ability to porcine CD80. The binding affinity of wild-type soluble human CTLA-4 is comparable to both human and porcine CD80. However, surprisingly, the soluble human CTLA-4-M97L mutant lost its binding ability to human CD80 and increased its ability to bind to porcine CD80, which indicates that the Met at the human CTLA-4 binding motif is extremely critical for its binding to human CD80.

Thus, in a first aspect, the invention provides mutant human Cytotoxic T-Lymphocyte-Associated Protein 4 (CTLA4) proteins comprising a sequence that is at least 80% identical to the full length of amino acids 39-152, e.g., 36-161, of SEQ ID NO:1, wherein the amino acid at position 134 is a Leucine.

In some embodiments, (i) the amino acid at position 113 is not Asparagine (N), and/or the amino and/or the amino acid at position 115 is neither Threonine (T) nor Serine (S); and (ii) the amino acid at position 145 is not Asparagine (N), and/or the amino and/or the amino acid at position 147 is neither Threonine (T) nor Serine (S).

In some embodiments, the amino acids at positions 113 and 145 are Alanine (A) or Glycine (G).

In another aspect, the invention provides mutant human CTLA4 fusion proteins comprising a first part comprising a mutant human Cytotoxic T-Lymphocyte-Associated Protein 4 (CTLA4) comprising a sequence that is at least 80% identical to the full length of amino acids 39-152, e.g., 36-161, of SEQ ID NO:1, wherein the amino acid at position 134 is a Leucine, and wherein optionally (i) the amino acid at position 113 is not Asparagine (N), and/or the amino and/or the amino acid at position 115 is neither Threonine (T) nor Serine (S); and (ii) the amino acid at position 145 is not Asparagine (N), and/or the amino and/or the amino acid at position 147 is neither Threonine (T) nor Serine (S); and a second part comprising an Fc region of a human immunoglobulin.

In some embodiments, the second part comprises the Fc region of human IgG.

In further aspects, the invention provides codon-optimized nucleic acid molecules (e.g., optimized for expression in a methylotrophic yeast, e.g., of the species *Pichia Pastoris*.) encoding a mutant human CTLA-4 described herein, or a fusion protein described herein, as well as vectors comprising the nucleic acid molecules, and host cells expressing the nucleic acid molecules. In some embodiments, the host cell is a methylotrophic yeast, e.g., of the species *Pichia Pastoris*.

In yet another aspect, the invention provides pharmaceutical compositions comprising the mutant human CTLA-4 proteins, or the fusion proteins, described herein, and a physiologically acceptable carrier.

In an additional aspect, the invention provides methods for inducing tolerance in a subject, e.g., a human subject, who has undergone or will undergo an organ transplantation procedure with a porcine organ. The methods include administering to the subject a therapeutically effective amount of a fusion protein described herein.

Also provided herein are fusion proteins for inducing tolerance to a transplanted organ of porcine origin, and the use of the fusion proteins described herein in the manufacture of a medicament for inducing tolerance to a transplanted organ of porcine origin.

In another aspect, the invention provides methods for producing a mutant human CTLA-4. The methods include expressing a mutant human CTLA-4 a sequence that is at least 80% identical to the full length of the amino acids 39-152, e.g., 36-161, of SEQ ID NO:1, wherein the amino acid at position 134 is a Leucine, and wherein optionally (i) the amino acid at position 113 is not Asparagine (N), and/or the amino acid at position 115 is neither Threonine (T) nor Serine (S); and (ii) the amino acid at position 145 is not Asparagine (N), and/or the amino acid at position 147 is neither Threonine (T) nor Serine (S), in a methylotrophic yeast; and substantially purifying the mutant human CTLA-4, thereby producing the composition.

In some embodiments, the methylotrophic yeast is of the species *Pichia Pastoris*.

The mutant human CTLA-4 based recombinant protein drugs, such as human CTLA-4-Ig, can be used and/or tested in a porcine model, whereas the use of porcine CTLA-4-based recombinant protein drugs such as porcine CTLA-4-Ig is restricted to porcine models. Porcine CTLA-4- and human CTLA-4-M97L mutant-based recombinant protein drugs can be used to specifically and only block the direct presentation by donor antigen presenting cell in pig to nonhuman primate xenotransplantation; the difference in binding specificity of CTLA-4 observed in this study are suitable for use in pig to human- or non-human primate xenotransplantation, as well as for studies such as pig to nonhuman primate xeno-transplantation. Human CTLA-4-M97L mutant-based recombinant protein drugs are ideal as they are likely to be non-immunogenic in human beings.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-C. Human CTLA-4-M97L mutant almost lost the ability to bind to human CD80. A) Flow cytometry binding analysis of human CTLA-4 wild-type (left panel) and human CTLA-4-M97L mutant (right panel) to the human CD80-expressing acute myelogenous leukemia cell line. Immunofluorescence staining was performed using biotinylated wild-type, mutant or anti-human CD80 mAb as the primary stain and PE-conjugated streptavidin (PE-SA) for the second stain. PE-SA only; biotinylated protein control [porcine CD3εγ ectodomain single-chain fusion protein (pCD3εγ)] [10]; isotype control [biotinylated mouse (BALB/c) IgG1, κ, clone# MOPC-21, Biolegend] were included. B) Bar graph presentation of the mean fluorescence intensity (MFI) from flow cytometry binding analysis data as described in A). Different concentrations of biotinylated pCD3εγ were used as non-specific fluorescence control. Error bars are included based on the calculated standard deviation. The hCTLA-4-M97L mutant's ability to bind to human CD80 was significantly decreased compared to the hCTLA-4-WT, $p<0.001$. C) Human CD80 blocking analysis by flow cytometry of the wild-type human CTLA-4 (left panel) and human CTLA-4-M97L mutant (right panel) with anti-human CD80 mAb (clone 2D10) to the human CD80-expressing acute myelogenous leukemia cell line. The concentration of the competitor is indicated. All figures of 1A-C are representatives of multiple individual experiments.

FIGS. 2A-C. Human CTLA-4-M97L mutant bound stronger to porcine CD80 compared to the wild-type. A) Flow cytometry binding analysis of human CTLA-4 (left panel) and human CTLA-4-M97L mutant (right panel) to the porcine CD80-expressing B-cell lymphoma line LCL 13271. PE-SA only, biotinylated protein control (pCD3εγ) [10]; isotype control [biotinylated Armenian hamster IgG, clone # HTK888, Biolegend] were included. B) Bar graph presentation of the MFI from flow cytometry binding analysis data as described in A). Different concentrations of biotinylated pCD3εγ were used as non-specific fluorescence control. Error bars are included based on the calculated standard deviation. The hCTLA-4-M97L mutant conferred stronger binding to porcine CD80 following the M97L mutation. C) CD80 blocking analysis by flow cytometry for human CTLA-4 (left panel) and human CTLA-4-M97L mutant (right panel) with anti-CD80 mAb (clone 16-10A1) to the porcine CD80-expressing B-cell lymphoma line LCL 13271. The concentration of the competitor is indicated. All data in this figure are representatives of multiple individual experiments.

FIGS. 3A-C. Porcine CTLA-4-L97M mutant obtained weak binding to human CD80. A) Flow cytometry binding analysis of porcine CTLA-4 (left panel) and porcine CTLA-4-L97M mutant (right panel) to the human CD80-expressing acute myelogenous leukemia cell line. PE-SA only; biotinylated protein control (pCD3εγ) [10]; isotype control [biotinylated mouse (BALB/c) IgG1, κ, clone# MOPC-21, Biolegend] were included. B) Bar graph presentation of the MFI from flow cytometry binding analysis data from A). Different concentrations of biotinylated pCD3εγ were used as non-specific fluorescence control. Error bars are included based on the calculated standard deviation. The pCTLA-4-L97M mutant conferred a weak but significant ability to bind to human CD80 compared to the pCTLA-4-WT, $p<0.05$. C) CD80 blocking analysis by flow cytometry for porcine CTLA-4 (left panel) and porcine CTLA-4-L97M mutant (right panel) with anti-human CD80 mAb (clone 2D10) to the human CD80-expressing acute myelogenous leukemia cell line. The concentration of the competitor is indicated. All figures in 3A-C are representatives of multiple individual experiments.

FIGS. 4A-C. Porcine CTLA-4-L97M mutant partially lost the binding ability to porcine CD80. A) Flow cytometry binding analysis of porcine CTLA-4 (left panel) and porcine CTLA-4-L97M mutant (right panel) to the porcine CD80-expressing B-cell lymphoma line LCL 13271. PE-SA only; biotinylated protein control (porcine CD3εγ) [10]; isotype control (biotinylated Armenian hamster IgG, clone #HTK888, Biolegend) were included. B) Bar graph presentation of the MFI from flow cytometry binding analysis data as described in A). Different concentrations of biotinylated pCD3εγ were used as non-specific fluorescence control. Error bars are included based on the calculated standard deviation. The pCTLA-4-L97M mutant's ability to bind to porcine CD80 was significantly decreased compared to the pCTLA-4-WT, $p<0.05$. C) Porcine CD80 blocking analysis by flow cytometry of porcine CTLA-4 (left panel) and porcine CTLA-4-L97M mutant (right panel) with anti-CD80 mAb (clone 16-10A1) to the porcine CD80-expressing B-cell lymphoma line LCL 13271. The concentration of the competitor is indicated. All figures in 4A-C are representatives of multiple individual experiments.

DETAILED DESCRIPTION

CTLA-4 is expressed on activated T cells and down regulates T cell proliferation and differentiation. The conserved mammalian CTLA-4 binding motif, MYPPPY (position 97-102) plays a critical role in binding to B7 [1, 2, 3]. Site directed mutagenesis demonstrated that while five single amino acid changes within this sequence partially inhibited the ability of CTLA-4 to bind to CD80, they completely abolished binding to CD86 [4]. Consistent with this, the mutant CTLA-4 sequence MYPPAA was unable to bind to CD80/CD86 in transgenic mice [5] and a similar sequence, MYPPPA, could not bind to CD80 expressing CHO cells [6]. However, further mutagenesis studies indicated that domains outside of this sequence also play a role in CTLA-4 binding. Single amino acid substitutions within the CDR1-like region of CTLA-4 that is located N-terminal to the MYPPPY prevented CTLA-4 from binding to CD80 and CD86 [4].

The porcine CTLA-4 binding motif is LYPPPY. It was reported that substituting L for M at position 134 (position 97 of the mature protein) inhibited the ability of porcine CTLA-4-Ig to bind to human CD80/CD86 [7]. The same group also showed that human and porcine CTLA-4-Ig were equally effective in binding to porcine CD86, suggesting that the leucine at position 97 is not necessary for the interaction of CTLA-4 and porcine CD86 [7].

Recently glycosylated and non-N-glycosylated soluble porcine CTLA-4 has been expressed and purified in yeast *Pichia pastoris*. While both isoforms bind to porcine CD80 on the porcine B cell lymphoma line LCL13271 with equal affinity (KD=13 nM), neither was able to bind to human CD80 [8]. As described herein, the L located within the binding motif of porcine CTLA-4 was mutated to the mammalian conserved M, and the M in the human binding motif was mutated to L. The effect of these single amino acid substitutions on the ability of these mutants to bind to porcine and human CD80 was evaluated by flow cytometry.

Mutant Human Cytotoxic T-Lymphocyte-Associated Protein 4 (CTLA4)

The proteins described herein comprise a mutant human CTLA-4 sequence. A number of human CTLA-4 sequences are known in the art and can be used in the constructs described herein. For example, all or part of the soluble human CTLA-4 sequence as set forth at GenBankAcc. Nos. NM_001037631.2 (nucleic acid) and NP_001032720.1 (amino acid) can be used.

In some embodiments, the amino acid sequence, including the M97L mutation, is as follows:

(SEQ ID NO: 1)

1 maclgfqrhk aqlnlatrtw pctllffllf ipvfcKAMHV

41 AQPAVVLASS RGIASFVCEY ASPGKATEVR VTVLRQADSQ

81 VTEVCAATYM MGNELTFLDD SICTGTSSGN QVNLTIQGLR

121 AMDTGLYICK VELLYPPPYY LGIGNGTQIY VIDPEPCPDS

161 D

In the sequence above, M97L is in bold; as this sequence retains the signal sequence (underlined), M97L is at position 134.

N-linked glycosylation sites (N113 and N145) are shown in bold and underlined. In some embodiments, one or both is mutated, e.g., to A.

In some embodiments, only the extracellular domain, e.g., at least amino acids 39-152, e.g., 36-161, of SEQ ID NO:1 are used.

Where less than all of SEQ ID NO:1 is used, the fragment must retain the ability to bind porcine CD80 and/or CD86.

In some embodiments, a CTLA-4 sequence lacking the signal sequence, e.g., lacking a sequence corresponding to amino acids 1-35, 1-36, 1-27, 1-38, or 1-39 of SEQ ID NO:1 is used. In some embodiments, a CTLA-4 sequence lacking the transmembrane domain, e.g., lacking amino acids corresponding to amino acids 153-174, or 163-174, of SEQ ID NO:1 is used. In some embodiments, a sequence lacking both a signal sequence and a transmembrane domain is used. In some embodiments, a sequence corresponding to amino acids 36-174 of SEQ ID NO: 1 are used; in some embodiments, a sequence corresponding to amino acids 39-152 of SEQ ID NO:1 are used; in some embodiments, the CTLA-4 sequence used comprises a fragment comprising a sequence corresponding to amino acids 134-139 of SEQ ID NO:1 that retains the ability to bind CD80 or CD86, and optionally a sequence corresponding to amino acids 58-131 (the IGv domain); and/or a sequence corresponding to amino acids 39-152 (the IgV_CTLA-4 domain). In some embodiments, a sequence as set forth in U.S. Pat. Nos. 5,851,795; 5,434,131; 5,885,579; 5,844,095; 5,968,510; 5,977,318; 5,885,796, or Larsen et al., 2005, Am J Transplant, 5:443-53, or fragment thereof lacking a signal sequence and/or transmembrane domain, is used.

In some embodiments, the methods include altering the CTLA-4 sequence to remove N-linked glycosylation sites. The consensus sequence for N-linked glycosylation is Asn-Xaa-[Ser/Thr]; disruption can be achieved by mutation of the Asn, or the Ser/Thr. Referring to SEQ ID NO: 1, above, there are N-linked glycosylation consensus sites at N113 and N145; disruption of these sites can be achieved by mutating N113 or T115, and N145 or T146. A mutation at N113 or N145 can be to any amino acid other than N, and a mutation at T115 or T146 can be to any amino acid other than T or S, so long as the mutation substantially preserves the CD80/CD86 binding ability, i.e., the mutant retains at least 20% of the affinity of the wild type molecule, e.g., at least 30%, 40%, 50%, 60%, 70%, 80%, 90%, 95%, or more of the function of the wild type molecule, e.g., in an in vitro assay as known in the art or described herein. In some embodiments, the mutations include N113A and N145A.

In some embodiments, the mutation is a conservative substitution. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III of US20110201052; pages 13-15 "Biochemistry" 2$^{nd}$ ED. Stryer ed (Stanford University); Henikoff et al., PNAS 1992 Vol 89 10915-10919; Lei et al., J Biol Chem 1995 May 19; 270(20):11882-6). In some embodiments, the protein includes a mutation at N113 and/or N145 to alanine or glycine. In some embodiments, the protein includes a mutation at N113 and/or N145 to a glutamine. In some embodiments, the protein includes a mutation at N113 and/or N145 to an aspartate or glutamate.

In some embodiments, instead of or in addition to a mutation at N113 or N145, the mutant includes a mutation at T115 and/or T146 to any amino acid other than serine or threonine, thereby disrupting the N-linked glycosylation consensus site. In some embodiments, the mutation at T115 and/or T146 is to alanine or glycine.

In some embodiments, the methods include introducing one or more additional mutations into the CTLA-4 sequence, e.g., L141E and/or A66Y (numbered with regard to SEQ ID NO:1) as described in Larsen et al., 2005, Am J Transplant, 5:443-53. Thus, in some embodiments, the sequence can be at least 80%, 85%, 90%, 95%, or 99% identical to at least 60%, 70%, 80%, 90%, or 100% of a soluble CTLA-4 sequence, e.g., SEQ ID NO:1; e.g., the sequence can include 1, 2, 3, 4, 5, 6, 7, 8, 9, 10, 11, 12, 13, 14, 15, 16, 17, 18, 19, or 20 mutations.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is typically at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. In another embodiment, the percent identity of two amino acid sequences can be assessed as a function of the conservation of amino acid residues within the same family of amino acids (e.g., positive charge, negative charge, polar and uncharged, hydrophobic) at corresponding positions in both amino acid sequences (e.g., the presence of an alanine residue in place of a valine residue at a specific position in both sequences shows a high level of conservation, but the presence of an arginine residue in place of an aspartate residue at a specific position in both sequences shows a low level of conservation).

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Fusion Proteins

In some embodiments, the recombinant CTLA-4 proteins described herein are fusion proteins, and include a non-CTLA-4 sequence fused to the N or C terminal of the CTLA-4.

In some embodiments, the non-CTLA-4 sequence is or comprises an Ig region, e.g., part of an immunoglobulin (preferably IgG) protein. Suitable sequences are known in the art. The Ig-region is typically derived from (i.e., based on a part of the sequence of) an immunoglobulin of a mammal. i.e., the species of the donee animal who is to receive the porcine xenotransplant, e.g., a mouse, a rat, a rabbit, guinea pig, cow, horse, or a human. Exemplary isotypes include mouse IgG1 (GenBank Accession No. M6042), mouse IgG2a (GenBank Accession No. BC018365), mouse IgG2b (GenBank Accession No. U62650 and BF135247), mouse IgG3 (GenBank Accession No. MMIGG10G), rat IgG2a (GenBank Accession No. BC088254), human IgG1 (GenBank Accession No AF237583), human IgG2 (GenBank Accession No. AY372691), human IgG3 (GenBank Accession No. M97802), and human IgG4 (GenBank Accession No. AF237586).

In some embodiments, a region of a human IgG is used that includes the hinge and CH2/CH3 regions, e.g., of human IgG1. See, e.g., U.S. Pat. No. 5,434,131A, U.S. Pat. No. 7,432,344B1, and Phelps et al., Xenotransplantation. 2009 November-December; 16(6):477-85.

In some embodiments, the Ig region is an Fc-region, e.g., the region of an immunoglobulin to which one or more polypeptides can bind. Examples of such polypeptides include protein A. e.g., protein A derived from the cell wall of *Staphylococcus aureus*, protein G, e.g., protein G derived from the cell wall of 3-hemolytic Streptococci, and/or protein L.

Peptide Tags

In some embodiments, the proteins or fusion proteins further include a peptide tag useful for purification. In some embodiments, the tag comprises histidines, e.g., two or more, e.g., three, four, five or six histidine residues at the C-terminus, and purification is achieved by binding to a nickel or cobalt column. An exemplary sequence including a 6His Tag is shown below. In some embodiments, the tag comprises glutathione-S-transferase (GST) and recovery is by affinity to substrate glutathione bound to a column, e.g. glutathione sepharose. In some embodiments, the tag comprises a FLAG peptide (e.g., N-DYKDDDDK-C(SEQ ID NO:2) or a variant thereof) and protein is recovered with specific antibody to the peptide. In some embodiments, the tag comprises an epitope derived from the Influenza protein hemagglutinin (HA) (e.g., N-YPYDVP-C(SEQ ID NO:3)) and protein is recovered using an anti-HA antibody that binds the epitope. In some embodiments, the tag comprises an epitope derived from the human proto-oncoprotein myc (e.g., N-ILKKATAYIL-C(SEQ ID NO:4), or N-EQKLISEEDL-C(SEQ ID NO:5)), and recovery is performed with an anti-myc antibody.

In some embodiments, the protein further comprises a proteolytic cleavage site between the purification tag and the CTLA-4 sequence, and after purification the protein is treated with the protease to remove the purification tag. Examples include the PreScission protease, thrombin, and factor Xa. Enterokinase sites that enable tag cleavage without leaving behind extra amino acids are preferred. In some embodiments, an exopeptidase is used to remove N-terminal His-tags (e.g., Qiagen TAGZyme). See, e.g., *The Recombinant Protein Handbook, Protein Amplification and Simple Purification*, Amersham Biosciences, available online at 130.15.90.245/methods/hand-books%20and%20manuals/the%20recombinant%20protein%20handbook.pdf.

Codon Optimization

In addition, the nucleic acid sequences used in the present methods are preferably codon-optimized for expression in a selected expression system. e.g., in *Pichia pastoris* (See, e.g., Woo et al., 2002). In order to optimize expression in non-mammalian cells, codon optimization specific for a selected host organism can be used. For example, in embodiments where *P. pastoris* is used as a host organism, the following Table 1 (source: kazusa.or.jp) can be used to select codons:

TABLE 1

| Codon Optimization Table for *Pichia Pastoris* | | | | |
| --- | --- | --- | --- | --- |
| triplet | UUU | UCU | UAU | UGU |
| amino acid | F | S | Y | C |
| fraction | 0.54 | 0.29 | 0.47 | 0.64 |
| frequency: per 1000 | 24.1 | 24.4 | 16.0 | 7.7 |
| (number) | (1963) | (1983) | (1300) | (626) |
| triplet | UUC | UCC | UAC | UGC |
| amino acid | F | S | Y | C |
| fraction | 0.46 | 0.20 | 0.53 | 0.36 |
| frequency: per 1000 | 20.6 | 16.5 | 18.1 | 4.4 |
| (number) | (1675) | (1344) | (1473) | (356) |

TABLE 1-continued

Codon Optimization Table for *Pichia Pastoris*

| triplet | UUA | UCA | UAA | UGA | GUG | GCG | GAG | GGG |
|---|---|---|---|---|---|---|---|---|
| amino acid | L | S | * | * | V | A | E | G |
| fraction | 0.16 | 0.18 | 0.51 | 0.20 | 0.19 | 0.06 | 0.44 | 0.10 |
| frequency: per 1000 | 15.6 | 15.2 | 0.8 | 0.3 | 12.3 | 3.9 | 29.0 | 5.8 |
| (number) | (1265) | (1234) | (69) | (27) | (998) | (314) | (2360) | (468) |
| triplet | UUG | UCG | UAG | UGG | | | | |
| amino acid | L | S | * | W | | | | |
| fraction | 0.33 | 0.09 | 0.29 | 1.00 | | | | |
| frequency: per 1000 | 31.5 | 7.4 | 0.5 | 10.3 | | | | |
| (number) | (2562) | (598) | (40) | (834) | | | | |
| triplet | CUU | CCU | CAU | CGU | | | | |
| amino acid | L | P | H | R | | | | |
| fraction | 0.16 | 0.35 | 0.57 | 0.17 | | | | |
| frequency: per 1000 | 15.9 | 15.8 | 11.8 | 6.9 | | | | |
| (number) | (1289) | (1282) | (960) | (564) | | | | |
| triplet | CUC | CCC | CAC | CGC | | | | |
| amino acid | L | P | H | R | | | | |
| fraction | 0.08 | 0.15 | 0.43 | 0.05 | | | | |
| frequency: per 1000 | 7.6 | 6.8 | 9.1 | 2.2 | | | | |
| (number) | (620) | (553) | (737) | (175) | | | | |
| triplet | CUA | CCA | CAA | CGA | | | | |
| amino acid | L | P | Q | R | | | | |
| fraction | 0.11 | 0.42 | 0.61 | 0.10 | | | | |
| frequency: per 1000 | 10.7 | 18.9 | 25.4 | 4.2 | | | | |
| (number) | (873) | (1540) | (2069) | (340) | | | | |
| triplet | CUG | CCG | CAG | CGG | | | | |
| amino acid | L | P | Q | R | | | | |
| fraction | 0.16 | 0.09 | 0.39 | 0.05 | | | | |
| frequency: per 1000 | 14.9 | 3.9 | 16.3 | 1.9 | | | | |
| (number) | (1215) | (320) | (1323) | (158) | | | | |
| triplet | AUU | ACU | AAU | AGU | | | | |
| amino acid | I | T | N | S | | | | |
| fraction | 0.50 | 0.40 | 0.48 | 0.15 | | | | |
| frequency: per 1000 | 31.1 | 22.4 | 25.1 | 12.5 | | | | |
| (number) | (2532) | (1820) | (2038) | (1020) | | | | |
| triplet | AUC | ACC | AAC | AGC | | | | |
| amino acid | I | T | N | S | | | | |
| fraction | 0.31 | 0.26 | 0.52 | 0.09 | | | | |
| frequency: per 1000 | 19.4 | 14.5 | 26.7 | 7.6 | | | | |
| (number) | (1580) | (1175) | (2168) | (621) | | | | |
| triplet | AUA | ACA | AAA | AGA | | | | |
| amino acid | I | T | K | R | | | | |
| fraction | 0.18 | 0.24 | 0.47 | 0.48 | | | | |
| frequency: per 1000 | 11.1 | 13.8 | 29.9 | 20.1 | | | | |
| (number) | (906) | (1118) | (2433) | (1634) | | | | |
| triplet | AUG | ACG | AAG | AGG | | | | |
| amino acid | M | T | K | R | | | | |
| fraction | 1.00 | 0.11 | 0.53 | 0.16 | | | | |
| frequency: per 1000 | 18.7 | 6.0 | 33.8 | 6.6 | | | | |
| (number) | (1517) | (491) | (2748) | (539) | | | | |
| triplet | GUU | GCU | GAU | GGU | | | | |
| amino acid | V | A | D | G | | | | |
| fraction | 0.42 | 0.45 | 0.58 | 0.44 | | | | |
| frequency: per 1000 | 26.9 | 28.9 | 35.7 | 25.5 | | | | |
| (number) | (2188) | (2351) | (2899) | (2075) | | | | |
| triplet | GUC | GCC | GAC | GGC | | | | |
| amino acid | V | A | D | G | | | | |
| fraction | 0.23 | 0.26 | 0.42 | 0.14 | | | | |
| frequency: per 1000 | 14.9 | 16.6 | 25.9 | 8.1 | | | | |
| (number) | (1210) | (1348) | (2103) | (655) | | | | |
| triplet | GUA | GCA | GAA | GGA | | | | |
| amino acid | V | A | E | G | | | | |
| fraction | 0.15 | 0.23 | 0.56 | 0.33 | | | | |
| frequency: per 1000 | 9.9 | 15.1 | 37.4 | 19.1 | | | | |
| (number) | (804) | (1228) | (3043) | (1550) | | | | |

Protein Production Methods

The methods for producing mutant human CTLA-4 proteins, e.g., fusion proteins, described herein can be performed using protein production methods known in the art. For example, for scaled-up production, fermentation expression can be used.

Furthermore, although in a preferred embodiment the present methods use *P. pastoris* as a host organism, e.g., wild-type, X33, GS115 (his4), KM71, MC100-3, SMD1163, SMD1165, or SMD1168 strain, others can also be used. For example, mutant strains of *P. pastoris* that have been altered to express proteins with more human-like glycosylation can be used (see, e.g., Bollok et al., Recent Patents on Biotechnology 2009, 3, 192-201; U.S. Pat. Nos. 7,029,872; 6,803,225; 7,449,308; 7,252,933; 7,326,681; 7,507,573; and references described therein); in such methods, either the wild-type human CTLA-4 or the mutant human CTLA-4 can be used. Other yeast, e.g., other methylotrophic yeast, e.g., yeast of the genera *Candida*, *Hansenula* or *Torulopsis*, can also be used. Generally speaking, most *P. pastoris* expression strains are derivatives of NRRL-Y 11430 (Northern Regional Research Laboratories, Peoria, Ill.).

Vectors suitable for use in the present methods are known in the art, and generally include a promoter, e.g., an AOX1, a constitutive *P. Pastoris* promoter derived from the *P. pastoris* glyceraldehyde-3-phosphate dehydrogenase gene (GAP) promoter, typically followed immediately with a DNA sequence that encodes a secretion signal, e.g., the *S. cerevisiae* α factor prepro signal sequence, or the signal sequence derived from the *P. pastoris* acid phosphatase gene (PHO1).

The vectors can also include one or more yeast selectable markers that can be used to identify and/or select those cells that contain the vector can be used. Such markers can include drug resistance markers and pathways for synthesis of essential cellular components, e.g., nutrients. Drug resistance markers that can be used in yeast include chloramphenicol, kanamycin, methotrexate, G418 (geneticin), Zeocin, and the like. Markers in synthesis pathways can be used with available yeast strains having auxotrophic mutations in the corresponding gene; examples include the pathways for synthesizing leucine (LEU2), tryptophan (TRP1 and TRP2), proline (PRO1), uracil (URA3, URA5, URA6), histidine (HIS3), lysine (LYS2), adenine (ADEJ or ADE2), and the like. Other yeast selectable markers include the ARR3 gene from *S. cerevisiae*, which confers arsenite resistance to yeast cells that are grown in the presence of arsenite (Bobrowicz et al., Yeast, 13:819-828 (1997); Wysocki et al, J-Biol. Chem. 272:30061-30066 (1997)). A number of suitable integration sites include those enumerated in U.S. Pat. No. 7,479,389 and include homologs to loci known for *Saccharomyces cerevisiae* and other yeast or fungi. Methods for integrating vectors into yeast are well known (See for example, U.S. Pat. No. 7,479,389, U.S. Pat. No. 7,514,253, U.S. Published Application No. 2009012400, and WO2009/085135). Examples of insertion sites include, but are not limited to, *Pichia* ADE genes; *Pichia* TRP (including TRP J through TRP2) genes; *Pichia* MCA genes; *Pichia* CYM genes: *Pichia* PEP genes; *Pichia* PRB genes; and *Pichia* LEU genes. The *Pichia* ADE1 and ARG4 genes have been described in Lin Cereghino et al, Gene 263:159-169 (2001) and U.S. Pat. No. 4,818,700, the HIS3 and TRP1 genes have been described in Cosano et al., Yeast 14:861-867 (1998), HIS4 has been described in GenBank Accession No. X5 180. See e.g., WO2011046855; Cregg. J. M. (2007) *Methods in Molecular Biology: Pichia Protocols*, Second Edition, Volume 389, Humana Press, Totowa, N.J.; Romanos et al., Yeast 8:423-488 (1992); Ilgen, et al., (2004) Chapter 7: *Pichia pastoris*. In: *Production of recombinant proteins: microbial and eukaryotic expression systems*. Gellissen, G (ed.) Wiley-VCH Verlag, Weinheim, Germany, pp. 143-162; Cereghino and Cregg, FEMS Microbiology Reviews 24:45-66 (2000); and Cregg, "The *Pichia* System", available online at pichia.com/pichia_system.pdf. Exemplary vectors include pPIC3K, pPIC9K, pAO815 and the pPICZ vector series.

Purification

Methods known in the art can be used for nickel-based purification of the mutant human CTLA-4 proteins, e.g., fusion proteins. For example, although the present examples use a hexahistidine tag to facilitate purification, this may not be preferred for a pharmaceutical intended for in vivo use. Thus, other methods, including ammonium sulfate precipitation, reversed phase chromatography, hydrophobic interaction chromatography (HIC), size exclusion chromatography, ion exchange chromatography, affinity chromatography, metal binding, immunoaffinity chromatography, HPLC, or purification tags (e.g., as described above) may be used to directly capture the purified proteins. See, e.g., Deutscher, M. P. (1990) Guide to Protein Purification. In: *Methods in Enzymology* (J. N. Abelson and M. I. Simon, eds.) Academic Press, San Diego, Calif.; and *The Recombinant Protein Handbook. Protein Amplification and Simple Purification*. Amersham Biosciences, available online at 130.15.90.245/methods/hand-books%20and%20manuals/the%20recombinant%20protein%20handbook.pdf.

After purification, the protein can optionally be concentrated. e.g., by lyophilization or ultrafiltration.

Methods of Use

CTLA-4 proteins, e.g., recombinant mutant CTLA-4 or CTLA-4 fusion proteins, described herein can be used in the treatment of certain disorders, e.g., transplant rejection, proteinuria, or autoimmune disease. Generally, the methods include administering a therapeutically effective amount of CTLA-4 proteins, e.g., CTLA-4 fusion proteins, as described herein, alone or in combination with another active agent, to a subject who is in need of, or who has been determined to be in need of, such treatment.

Xenotransplant Tolerance

The CTLA-4 proteins, e.g., CTLA-4 fusion proteins, described herein can be used to induce tolerance in a subject who is undergoing or who has undergone transplant with a xenogeneic organ, tissue, or cells, e.g., a solid organ, tissue, bone marrow, or blood cells, i.e., from a pig. For example, the methods can be used in a wide variety of tissue and organ transplant procedures, e.g., the methods can be used to induce tolerance in a recipient of a graft of a porcine tissue or organ such as pancreatic islets, liver, kidney, heart, lung, skin, muscle, neuronal tissue, stomach, and intestines. Thus, the new methods can be applied in treatments of diseases or conditions that entail porcine tissue or organ transplantation (e.g., liver transplantation to treat liver failure, transplantation of muscle cells to treat muscular dystrophy, or transplantation of neuronal tissue to treat Huntington's disease or Parkinson's disease) into a non-porcine mammal, e.g., a human or non-human, non-porcine mammal. In some embodiments, the methods include identifying, and then administering to, a subject in need of treatment. Tolerance to donor antigen can be evaluated by known methods, e.g., by MLR assays or cell-mediated lympholysis (CML) assays. In some embodiments, the methods include the use of the proteins or fusion proteins described herein to reduce ischemia/reperfusion injury associated with organ retrieval and storage influences the development of chronic graft dysfunction (Takada et al., J Clin Invest. 1997, 100(5):1199-203). In some embodiments, the proteins or fusion proteins are administered before, during, and/or after the transplant procedure.

Pharmaceutical Compositions and Methods of Administration

The methods described herein include the manufacture and use of pharmaceutical compositions, which include CTLA-4 proteins, e.g., CTLA-4 fusion proteins, as described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Thus the present invention can include compositions comprising both a CTLA-4 proteins, e.g., CTLA-4 fusion proteins, as described herein and an additional active compound, e.g., in therapeutically relevant or effective amounts.

Pharmaceutical compositions are typically formulated to be compatible with the intended route of administration. Examples of routes of administration include parenteral, e.g., intravenous, intradermal, intramuscular, subcutaneous, oral (e.g., inhalation), transdermal (topical), and transmucosal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Materials and Methods

The following materials and methods were used in the Examples set forth below.

The leucine at position 97 of the non-N-glycosylated wild-type porcine CTLA-4 (pCTLA-4-Non-N-Gly in pwPICZalpha) [8] was replaced with methionine using the QuickChange site-directed mutagenesis kit (Stratagene). The site-directed mutagenesis primers are L97M For (5' TAC ATC TGT AAG GTC GAA TTG ATG TAC CCA CCT CCA TAC TAC GTT 3'; SEQ ID NO:6) and L97M Rev (5' AAC GTA GTA TGG AGG TGG GTA CAT CAA TTC GAC CTT ACA GAT GTA 3'; SEQ ID NO:7). The mutant construct was confirmed by DNA sequencing analysis. Using the exact same strategy as described above the methionine at position 97 of the non-N-glycosylated wild-type human CTLA-4 (hCTLA-4-Non-N-Gly in pwPICZalpha, which was constructed as described for pCTLA-4-Non-N-Gly in pwPICZalpha [8]) was replaced with leucine. The forward PCR primer is M134L. For (5' TAC ATT TGT AAG GTT GAG TTG TTG TAC CCA CCT CCA TAC TAC TTG 3'; SEQ ID NO:8) and the reverse PCR primer is M134L Rev (5' CAA GTA GTA TGG AGG TGG GTA CAA CAA CTC AAC CTT ACA AAT GTA 3'; SEQ ID NO:9).

The final sequences are as follows:

Non-N-Glycosylated soluble human CTLA-4-6×His amino acid sequence (aa 36-161)

(SEQ ID NO: 10)
KAMHVAQPAVVLASSRGIASFVCEYASPGKATEVRVTVLRQADSQVT

EVCAATYMMGNELTFLDDSICTGTSSGNQV<u>A</u>LTIQGLRAMDTGLYIC

KVELMYPPPYYLGIG<u>A</u>GTQIYVIDPEPCPDSDHHHHHH

Non-N-Glycosylated soluble human CTLA-4-6×His DNA sequence (SEQ ID NO: 11)
AAG GCT ATG CAC GTT GCT CAA CCA GCT GTT GTC TTG

GCT TCT TCC AGA GGT ATT GCT TCT TTC GTT TGT GAG

TAC GCT TCT CCA GGT AAG GCT ACT GAG GTT AGA GTT

ACT GTC TTG AGA CAA GCT GAC TCT CAA GTT ACT GAG

GTT TGT GCT GCT ACT TAC ATG ATG GGT AAC GAG TTG

ACT TTC TTG GAC GAC TCT ATT TGT ACT GGT ACT TCT

TCC GGT AAC CAA GTT gct TTG ACT ATT CAA GGT TTG

AGA GCT ATG GAC ACT GGT TTG TAC ATT TGT AAG GTT

GAG TTG ATG TAC CCA CCT CCA TAC TAC TTG GGT ATT

GGT gct GGT ACT CAA ATT TAC GTT ATT GAC CCA GAG

CCT TGT CCA GAC TCT GAC CAC CAC CAC CAC CAC CAC

Non-N-Glycosylated soluble human CTLA-4-M97L-6×His amino acid sequence (aa 36-161)

(SEQ ID NO: 12)
KAMHVAQPAVVLASSRGIASFVCEYASPGKATEVRVTVLRQADSQVT

EVCAATYMMGNELTFLDDSICTGTSSGNQV<u>A</u>LTIQGLRAMDTGLYIC

KVEL<u>L</u>YPPPYYLGIG<u>A</u>GTQIYVIDPEPCPDSDHHHHHH

Non-N-Glycosylated soluble human CTLA-4-M97L-6×His DAN sequence (SEQ ID NO: 13)
AAG GCT ATG CAC GTT GCT CAA CCA GCT GTT GTC TTG

GCT TCT TCC AGA GGT ATT GCT TCT TTC GTT TGT GAG

TAC GCT TCT CCA GGT AAG GCT ACT GAG GTT AGA GTT

```
-continued
ACT GTC TTG AGA CAA GCT GAC TCT CAA GTT ACT GAG

GTT TGT GCT GCT ACT TAC ATG ATG GGT AAC GAG TTG

ACT TTC TTG GAC GAC TCT ATT TGT ACT GGT ACT TCT

TCC GGT AAC CAA GTT gct TTG ACT ATT CAA GGT TTG

AGA GCT ATG GAC ACT GGT TTG TAC ATT TGT AAG GTT

GAG TTG ttg TAC CCA CCT CCA TAC TAC TTG GGT ATT

GGT gct GGT ACT CAA ATT TAC GTT ATT GAC CCA GAG

CCT TGT CCA GAC TCT GAC CAC CAC CAC CAC CAC CAC
```

Protein expression and purification in *Pichia pastoris* and Western blot analysis were performed as previously described [8]. FACS binding and blocking analysis was performed as previously described for the wild-type porcine CTLA-4 [8] using a porcine CD80-expressing B-cell lymphoma line LCL13271 [9] and human CD80-expressing acute myelogenous leukemia cell line (Cat#CRL-2740, ATCC, Manassas, Va.).

Example 1. Soluble Human CTLA-4-M97L Mutant does not Bind to Human CD80

The porcine CTLA-4 binding motif is LYPPPY, and soluble porcine CTLA-4 does not bind human CD80 [8]; therefore, it was hypothesized that substituting M for L might decrease or abolish the binding ability of the soluble human CTLA-4 to human CD80. As shown in FIGS. 1A-B, the wild-type soluble human CTLA-4 bound to human CD80 very well. In contrast, the human CTLA-4-M97L mutant has no or significantly reduced binding to human CD80 following the single amino acid mutation. These results demonstrated that M at position 97 is extremely critical in determining the ability of human CTLA-4 to bind to human CD80. To confirm the binding specificity, a human CD80 blocking assay was performed in which the unlabeled mutant or wild-type soluble human CTLA-4 were added to the cells first followed by addition of a biotinylated anti-human CD80 mAb. As shown in FIG. 1C, the wild-type soluble human CTLA-4 blocked the binding of an anti-human CD80 mAb to human CD80 in a dose dependent manner. However the M97L mutant almost completely failed to block the binding of the same mAb suggesting that the single amino acid mutation caused a loss in binding function to human CD80. The results from this blocking analysis confirmed that the binding of the wild-type human CTLA-4 is specific to human CD80.

Example 2. Soluble Human CTLA-4-M97L Mutant Improved its Binding Ability to Porcine CD80

Figure 2C:
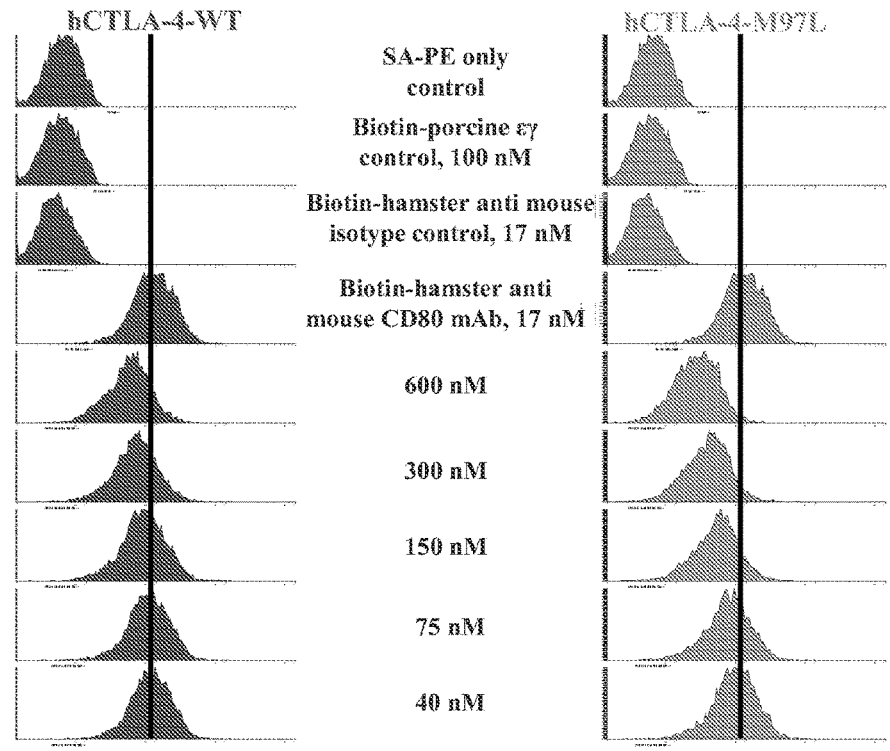

It was hypothesized that the soluble human CTLA-4-M97L mutant will bind to porcine CD80 more strongly than the wild-type soluble human CTLA-4. As shown in FIGS. 2A-B, both wild-type hCTLA4 and mutant hCTLA-4-M97L bound to porcine CD80 very well, with the mutant showing a stronger affinity for porcine CD80 than the wild-type. FACS blocking analysis of the binding for the hamster anti-mouse CD80 mAb to porcine CD80 demonstrated that both wild-type and the M97L mutant blocked the binding in a dose dependent manner (FIG. 2C).

Example 3. Soluble Porcine CTLA-4-L97M Mutant Obtained Weak Binding to Human CD80

As noted above, the soluble porcine CTLA-4 does not bind human CD80 (left panel of FIG. 3A and [8].

However, as shown in right panel of FIGS. 3A-B, the soluble porcine CTLA-4-L97M mutant was able to bind to human CD80, although with very low affinity. Blocking analysis by flow cytometry also showed that the soluble porcine CTLA-4-L97M mutant was capable, albeit very weakly, of blocking the binding of an anti-human CD80 mAb to human CD80 (FIG. 3C). These results indicate that the soluble porcine CTLA-4-L97M mutant obtained the ability to very weakly bind to human CD80 following the single amino acid mutation.

Example 4. Soluble Porcine CTLA-4-L97M Mutant Decreased its Binding Ability to Porcine CD80

Figure 4B:
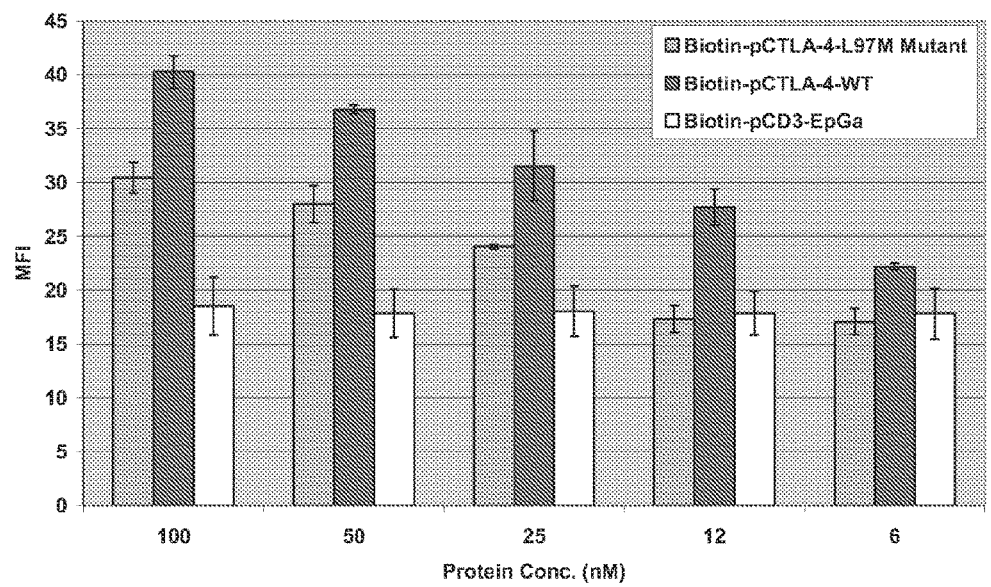
Figure 4B:
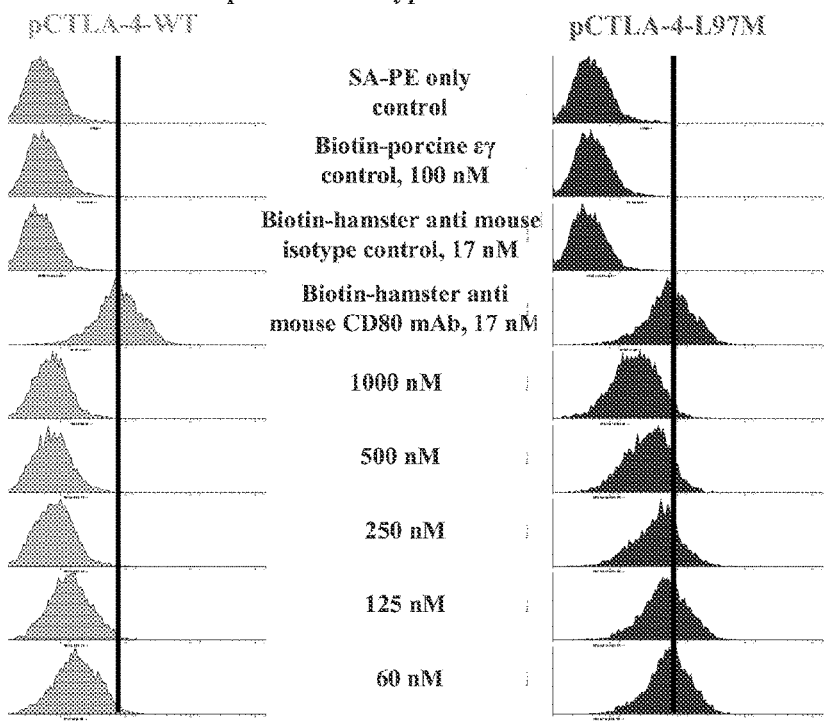

As shown in the right panel of FIGS. 4A-B, the soluble porcine CTLA-4-L97M mutant bound to porcine CD80 with lower affinity than its wild-type. Blocking analysis by flow cytometry also showed L97M had decreased ability to block binding of hamster anti-mouse CD80 mAb to porcine CD80 (right panel of FIG. 4C). These data demonstrated that the L at position 97 of porcine CTLA-4 is important for determining binding to porcine CD80.

In summary, the M at position 97 of human CTLA-4 is extremely critical for its binding to human CD80 and the L at position 97 of porcine CTLA-4 is also very important for porcine CTLA-4 binding to porcine CD80 (Table 2). These data suggest that human CTLA-4-based recombinant protein drugs can be tested in porcine models.

Porcine CTLA-4- and human CTLA-4-M97L mutant-based recombinant protein drugs can be used to specifically only block the direct presentation by donor antigen presenting cells in pig to human or nonhuman primate xeno-transplantation. Human CTLA-4-M97L mutant based recombinant drugs will be more ideal as it is without immunogenicity to human being.

TABLE 2

Cross-species binding of the soluble human CTLA-4 versus soluble porcine CTLA-4

| | Soluble human CTLA-4 | | Soluble porcine CTLA-4 | |
|---|---|---|---|---|
| | WT | M97L | WT | L97M |
| Human CD80 | ++++ | ≤+ | − | + |
| Porcine CD80 | ++++ | +++++ | ++++ | ++ |

Note:
binding percentage of the wild-type was presented as +++++ (125%), ++++ (100%), +++ (75%), ++ (50%), + (25%), ≤+ (less than 25%), − (no binding).

REFERENCES

[1] Riha P, Rudd C E, CD28 co-signaling in the adaptive immune response. Self Nonself 2010; 1:231-240.

[2] Sansom D M, CD28, CTLA-4 and their ligands: who does what and to whom? Immunology 2000; 101:169-177.

[3] Bour-Jordan H, Esensten J H, Martinez-Llordella M, Penaranda C, Stumpf M, Bluestone J A. Intrinsic and extrinsic control of peripheral T-cell tolerance by costimulatory molecules of the CD28/B7 family. Immunol Rev 2011; 241:180-205.

[4] Morton P A, Fu X T, Stewart J A, Giacoletto K S, White S L, Leysath C E, Evans R J, Shieh J J, Karr R W. Differential effects of CTLA-4 substitutions on the binding of human CD80 (B7-1) and CD86 (B7-2). J Immunol 1996; 156:1047-54.

[5] Chikuma S, Abbas A K, Bluestone J A. B7-independent inhibition of T cells by CTLA-4. J Immunol 2005; 175: 177-81.
[6] Pentcheva-Hoang T, Egen J G, Wojnoonski K, Allison J P. B7-1 and B7-2 selectively recruit CTLA-4 and CD28 to the immunological synapse. Immunity 2004; 21:401-13.
[7] Vaughan A N, Malde P, Rogers N J, Jackson I M, Lechler R I, Dorling A. Porcine CTLA4-Ig lacks a MYPPPY motif, binds inefficiently to human B7 and specifically suppresses human CD4+ T cell responses costimulated by pig but not human B7. J Immunol 2000; 165:3175-81.
[8] Peraino J, Zhang H, Hermanrud C E, Li G, Sachs D H, Huang C A, Wang Z. Expression and purification of soluble porcine CTLA-4 in yeast *Pichia pastoris*. Protein Expr Purif 2012; 82:270-8.
[9] Cho P S, Lo D P, Wikiel K J, Rowland H C, Coburn R C, McMorrow I M, Goodrich J G, Am J S, Billiter R A, Houser S L, Shimizu A, Yang Y G, Sachs D H, Huang C A, Establishment of transplantable porcine tumor cell lines derived from MHC-inbred miniature swine. Blood 2007; 110: 3996-4004.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A mutant human Cytotoxic T-Lymphocyte-Associated Protein 4 (CTLA4) protein comprising a sequence that is at least 95% identical to the full length of amino acids 39-152 of SEQ ID NO:1, wherein the amino acid at position 134 is a Leucine, wherein the protein binds porcine B7 and does not bind human B7.

2. The mutant human CTLA4 protein of claim 1, wherein
   (i) the amino acid at position 113 is not Asparagine (N), and/or the amino acid at position 115 is neither Threonine (T) nor Serine (S); and
   (ii) the amino acid at position 145 is not Asparagine (N), and/or the amino acid at position 147 is neither Threonine (T) nor Serine (S).

3. The mutant human CTLA4 protein of claim 2, wherein the amino acids at positions 113 and 145 are Alanine (A) or Glycine (G).

4. The mutant human CTLA4 protein of claim 1, which is at least 95% identical to the full length of amino acids 36-161 of SEQ ID NO:1, wherein the amino acid at position 134 is a Leucine.

5. A mutant human CTLA4 fusion protein comprising:
   a first part comprising a mutant human Cytotoxic T-Lymphocyte-Associated Protein 4 (CTLA4) comprising a sequence that is at least 95% identical to the full length of amino acids 39-152 of SEQ ID NO:1, wherein the amino acid at position 134 is a Leucine, wherein the protein binds porcine B7 and does not bind human B7, and wherein optionally
   (i) the amino acid at position 113 is not Asparagine (N), and/or the amino acid at position 115 is neither Threonine (T) nor Serine (S); and
   (ii) the amino acid at position 145 is not Asparagine (N), and/or the amino acid at position 147 is neither Threonine (T) nor Serine (S); and
   a second part comprising an Fc region of a human immunoglobulin.

6. The fusion protein of claim 5, wherein the second part comprises the Fc region of human IgG.

7. The fusion protein of claim 5, wherein the mutant human Cytotoxic T-Lymphocyte-Associated Protein 4

(CTLA4) is at least 95% identical to the full length of amino acids 36-161 of SEQ ID NO:1, wherein the amino acid at position 134 is a Leucine.

8. A codon-optimized nucleic acid molecule encoding the mutant human CTLA-4 of claim 1, wherein the nucleic acid molecule is optimized for expression in a non-mammalian host cell.

9. A vector comprising the nucleic acid molecule of claim 8.

10. A non-mammalian host cell expressing the nucleic acid molecule of claim 8.

11. The non-mammalian host cell of claim 10, wherein the non-mammalian host cell is a methylotrophic yeast.

12. The non-mammalian host cell of claim 11, wherein the non-mammalian host cell is a cell of the species *Pichia Pastoris*.

13. A pharmaceutical composition comprising the mutant human CTLA-4 of claim 1, and a physiologically acceptable carrier.

14. A method of treating transplant rejection in a human subject who has undergone or will undergo an organ transplantation procedure with a porcine organ, the method comprising administering to the subject a therapeutically effective amount of the fusion protein of claim 5.

15. A method of producing a mutant human CTLA-4, the method comprising:
    expressing a mutant human CTLA-4 comprising a sequence that is at least 95% identical to the full length of amino acids 39-152 of SEQ ID NO:1, wherein the amino acid at position 134 is a Leucine, wherein the protein binds porcine B7 and does not bind human B7, and wherein optionally
    (i) the amino acid at position 113 is not Asparagine (N), and/or the amino acid at position 115 is neither Threonine (T) nor Serine (S); and
    (ii) the amino acid at position 145 is not Asparagine (N), and/or the amino acid at position 147 is neither Threonine (T) nor Serine (S),
    in a methylotrophic yeast; and
    substantially purifying the human CTLA-4,
    thereby producing the mutant human CTLA-4.

16. The method of claim 15, wherein the methylotrophic yeast is of the species *Pichia Pastoris*.

17. The method of claim 15, wherein the mutant human CTLA4 is at least 95% identical to the full length of amino acids 36-161 of SEQ ID NO:1, wherein the amino acid at position 134 is a Leucine.

18. A codon-optimized nucleic acid molecule encoding the mutant human CTLA-4 fusion protein of claim 5, wherein the nucleic acid molecule is optimized for expression in a non-mammalian host cell.

19. A pharmaceutical composition comprising the mutant human CTLA-4 fusion protein of claim 5, and a physiologically acceptable carrier.

\* \* \* \* \*